Patented Mar. 23, 1954

Plant Pat. 1,265

UNITED STATES PATENT OFFICE 1,265

NECTARINE TREE

Frederic W. Anderson, Merced, Calif.

No Drawing. Application March 17, 1953, Serial No. 343,004

1 Claim. (Cl. 47—62)

The present invention is directed to a new and distinct variety of nectarine tree which bears yellow fleshed, clingstone fruit.

For a number of years I have conducted an extensive plant breeding program for the origination of commercially desirable nectarine trees; this program having been carried out in my experimental orchard near Le Grand, Merced County, California.

One of the primary aims of such program has been the origination of a series of new and distinct nectarine varieties having different ripening periods, but which periods are sufficiently related that a relatively long harvest season of nectarine fruit may be attained by the planting of a number of such varieties.

Examples of the varieties of such nectarine trees heretofore invented and patented by me, with their approximate ripening periods (1952) in my experimental orchard, located as above, are as follows:

Early Le Grand, United States Plant Patent 980—July 7th to 17th.

Red Grand, United States Plant Patent 1,060—July 20th to August 2nd.

Le Grand, United States Plant Patent 549—July 24th to August 5th.

Late Le Grand, United States Plant Patent 1035—August 12th to 25th.

The instant variety of nectarine tree provides a ripening period which supplies the trade with fruit at a time between the end of the harvest of the Le Grand nectarine and the beginning of the harvest of the Late Le Grand nectarine; the present variety having a ripening period beginning approximately one week later than the Le Grand nectarine and approximately one week earlier than the Late Le Grand nectarine. Thus, the present variety effectively fills the gap, in the continuity of harvest of the several identified varieties of my nectarines, previously existent between the Le Grand nectarine and the Late Le Grand nectarine.

The new and distinct variety of nectarine tree here claimed was originated and asexually reproduced by me in my experimental orchard near Le Grand, county of Merced, California, in the following manner:

A substantial number of seedlings were grown by me in such orchard from seeds resulting from self- and cross-pollinated flowers of the Le Grand nectarine. These seedlings were maintained under careful observation and records kept thereof; the present variety having been a selection of one of the above seedlings as it evidenced the desirable ripening period intermediate the Le Grand nectarine and the Late Le Grand nectarine.

Subsequent to its discovery the present variety of nectarine tree was top-worked, on mature stock, in my identified orchard, and on the same day there was also top-worked onto such root stock, the Le Grand nectarine and the Late Le Grand nectarine. When these top-workings came into bearing it was found that they all had tree characteristics closely resembling each other, and all bore commercially desirable fruit of similar physical characteristics, but that the present variety maintained its intermediate ripening period relative to the other two identified varieties. Subsequent asexual reproductions of the present variety of nectarine tree establish that such characteristic remains true.

Thus, while the present variety of nectarine has tree and fruit characteristics which closely resemble those of the Le Grand and Late Le Grand nectarines, the major distributing characteristic is its ripening period; to-wit, ripening approximately one week later than the Le Grand and approximately one week earlier than the Late Le Grand nectarine.

Another distinctive characteristic of the present variety of nectarine is that the seeds or kernels are sweet, while the Le Grand and Late Le Grand nectarines have the usual bitter kernels so normal to peach and nectarine varieties.

The tree and its fruit of the present variety may vary in slight detail due to climatic and soil conditions under which the variety may be grown.

Having thus described my invention, I claim:

A new and distinct variety of nectarine tree, as described, characterized—in comparison to the Le Grand and Late Le Grand nectarines—by similar tree and fruit characteristics, but distinguished by a ripening period approximately one week later than the Le Grand nectarine and approximately one week earlier than the Late Le Grand nectarine, and by sweet kernels.

FREDERIC W. ANDERSON.

No references cited.